US008093445B2

(12) United States Patent
Sigurjonsson et al.

(10) Patent No.: US 8,093,445 B2
(45) Date of Patent: *Jan. 10, 2012

(54) WOUND DRESSING AND METHOD FOR MANUFACTURING THE SAME

(75) Inventors: Gudmundur Fertram Sigurjonsson, Christchurch (NZ); Thordur Elefsen, Mosfellsbaer (IS); Palmar Gudnason, Mosfellsbaer (IS)

(73) Assignee: Ossur HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 12/259,453

(22) Filed: Oct. 28, 2008

(65) Prior Publication Data

US 2009/0124950 A1     May 14, 2009

Related U.S. Application Data

(63) Continuation of application No. 11/136,465, filed on May 25, 2005, now Pat. No. 7,531,711, which is a continuation-in-part of application No. 10/924,861, filed on Aug. 25, 2004, now Pat. No. 7,396,975.

(60) Provisional application No. 60/503,546, filed on Sep. 17, 2003, provisional application No. 60/518,317, filed on Nov. 10, 2003, provisional application No. 60/543,401, filed on Feb. 11, 2004.

(51) Int. Cl.
*A61F 13/00* (2006.01)
*A61F 2/00* (2006.01)
*A61F 15/00* (2006.01)

(52) U.S. Cl. ............... 602/54; 602/41; 602/42; 602/43; 602/47; 602/55; 602/56; 602/58; 128/888; 424/443; 424/445

(58) Field of Classification Search .............. 602/41–59; 424/443–449; 128/888–889; 206/440–441
See application file for complete search history.

(56) References Cited

U.S. PATENT DOCUMENTS

| 2,390,184 A | 12/1945 | Seng |
| 2,649,088 A | 8/1953 | Sigg |
| 2,764,976 A | 10/1956 | Skiles |
| 3,006,338 A | 10/1961 | Davies |
| 3,042,549 A | 7/1962 | Arnold |

(Continued)

FOREIGN PATENT DOCUMENTS

CA     724612     12/1965

(Continued)

OTHER PUBLICATIONS

Donatas Satas, ed., Advances in Pressure Sensitive Adhesive Technology 2, pp. 724-746. 1995.

(Continued)

*Primary Examiner* — Patricia Bianco
*Assistant Examiner* — Brandon Jackson
(74) *Attorney, Agent, or Firm* — Bacon & Thomas, PLLC

(57) ABSTRACT

A wound dressing defines bodyside and backside surfaces. The dressing comprises a backing layer defining a center portion and a border portion surrounding the center portion. An absorbent core is connected to a surface of the backing layer within the center portion The absorbent core may be exposed along a bodyside surface of the wound dressing, or various adhesives and non-adhesive substrates may be applied along a surface of the absorbent core so as to define part of the bodyside surface of the wound dressing.

13 Claims, 10 Drawing Sheets

U.S. PATENT DOCUMENTS

| | | |
|---|---|---|
| 3,113,568 A | 12/1963 | Robins |
| 3,156,242 A | 11/1964 | Crowe, Jr. |
| 3,292,619 A | 12/1966 | Egler |
| 3,307,545 A | 3/1967 | Surowitz |
| 3,439,676 A | 4/1969 | Burda |
| 3,616,156 A | 10/1971 | Scholl |
| 3,645,835 A | 2/1972 | Hodgson |
| 3,678,933 A | 7/1972 | Moore et al. |
| 3,814,101 A | 6/1974 | Kozak |
| 3,927,669 A | 12/1975 | Glatt |
| 3,972,328 A | 8/1976 | Chen |
| 4,034,751 A | 7/1977 | Hung |
| 4,055,180 A | 10/1977 | Karami |
| 4,175,557 A | 11/1979 | Hung |
| 4,212,296 A | 7/1980 | Schaar |
| 4,349,020 A | 9/1982 | Krikorian |
| 4,360,021 A | 11/1982 | Stima |
| 4,373,519 A | 2/1983 | Errede et al. |
| 4,408,996 A | 10/1983 | Baldwin |
| 4,538,603 A | 9/1985 | Pawelchak et al. |
| 4,560,372 A | 12/1985 | Pieniak |
| 4,603,076 A | 7/1986 | Bowditch et al. |
| 4,614,183 A | 9/1986 | McCracken et al. |
| 4,635,624 A | 1/1987 | Gilman |
| 4,653,492 A | 3/1987 | Parsons |
| 4,655,210 A | 4/1987 | Edenbaum et al. |
| 4,657,006 A | 4/1987 | Rawlings et al. |
| 4,661,099 A | 4/1987 | von Bittera |
| 4,664,106 A | 5/1987 | Snedeker |
| 4,684,557 A | 8/1987 | Pennace |
| 4,690,683 A | 9/1987 | Chien |
| 4,699,146 A | 10/1987 | Sieverding |
| 4,733,659 A | 3/1988 | Edenbaum et al. |
| 4,738,257 A | 4/1988 | Meyer et al. |
| 4,750,482 A | 6/1988 | Sieverding |
| 4,753,231 A | 6/1988 | Lang et al. |
| D296,838 S | 7/1988 | Diaz |
| 4,762,680 A | 8/1988 | Pennace |
| 4,773,408 A | 9/1988 | Cilento et al. |
| 4,838,253 A | 6/1989 | Brassington et al. |
| 4,846,164 A | 7/1989 | Martz |
| 4,860,737 A | 8/1989 | Lang et al. |
| 4,867,748 A | 9/1989 | Samuelsen |
| 4,906,240 A | 3/1990 | Reed et al. |
| 4,921,704 A | 5/1990 | Fabo |
| 4,950,148 A | 8/1990 | Nakanishi |
| 4,960,477 A | 10/1990 | Mesek |
| 4,977,892 A | 12/1990 | Ewall |
| 4,985,277 A | 1/1991 | Shimizu et al. |
| 4,991,574 A | 2/1991 | Pocknell |
| 4,995,382 A | 2/1991 | Lang et al. |
| 5,010,883 A | 4/1991 | Rawlings et al. |
| 5,074,944 A | 12/1991 | Trenka |
| 5,088,483 A | 2/1992 | Heinecke |
| 5,147,338 A | 9/1992 | Lang et al. |
| 5,160,328 A | 11/1992 | Cartmell et al. |
| 5,167,613 A | 12/1992 | Karami et al. |
| 5,209,801 A | 5/1993 | Smith |
| 5,279,890 A | 1/1994 | Ikeno |
| 5,322,729 A | 6/1994 | Heeter |
| 5,340,363 A | 8/1994 | Fabo |
| 5,352,508 A | 10/1994 | Cheong |
| 5,362,508 A | 11/1994 | Wheeler |
| 5,395,305 A | 3/1995 | Koide et al. |
| 5,409,472 A | 4/1995 | Rawlings et al. |
| 5,445,604 A | 8/1995 | Lang |
| 5,486,158 A | 1/1996 | Samuelsen |
| 5,489,262 A | 2/1996 | Cartmell et al. |
| 5,512,041 A | 4/1996 | Bogart |
| 5,540,922 A | 7/1996 | Fabo |
| 5,556,375 A | 9/1996 | Ewall |
| 5,571,529 A | 11/1996 | Cheong |
| 5,591,820 A | 1/1997 | Kydonieus et al. |
| 5,593,395 A | 1/1997 | Martz |
| 5,603,946 A | 2/1997 | Constantine |
| 5,607,388 A | 3/1997 | Ewall |
| 5,629,014 A | 5/1997 | Kwiatek et al. |
| 5,633,007 A | 5/1997 | Webb et al. |
| 5,635,201 A | 6/1997 | Fabo |
| 5,653,699 A | 8/1997 | Reed et al. |
| 5,681,579 A | 10/1997 | Freeman |
| 5,738,642 A | 4/1998 | Heinecke |
| 5,759,560 A | 6/1998 | Dillon |
| 5,782,787 A | 7/1998 | Webster |
| 5,847,003 A | 12/1998 | Ptchelintsev et al. |
| 5,891,076 A | 4/1999 | Fabo |
| 5,914,125 A | 6/1999 | Andrews et al. |
| 5,919,476 A | 7/1999 | Fischer |
| 5,925,439 A | 7/1999 | Haubach |
| 5,941,840 A | 8/1999 | Court et al. |
| 5,942,332 A | 8/1999 | Nakamura |
| 5,973,221 A | 10/1999 | Collyer et al. |
| 5,981,822 A | 11/1999 | Addison |
| 6,040,492 A | 3/2000 | Lindquist et al. |
| 6,051,317 A | 4/2000 | Brueggemann et al. |
| 6,051,747 A | 4/2000 | Lindqvist et al. |
| 6,066,773 A | 5/2000 | Freeman |
| 6,103,369 A | 8/2000 | Lucast et al. |
| 6,107,536 A | 8/2000 | Dadinis |
| D433,140 S | 10/2000 | Nielsen |
| 6,136,039 A | 10/2000 | Kristonsson et al. |
| 6,149,614 A | 11/2000 | Dunshee et al. |
| 6,200,195 B1 | 3/2001 | Furuno |
| 6,207,875 B1 | 3/2001 | Lindqvist et al. |
| 6,242,665 B1 | 6/2001 | Malowaniec |
| 6,291,050 B1 | 9/2001 | Cree |
| 6,320,093 B1 * | 11/2001 | Augustine et al. .............. 602/41 |
| 6,333,093 B1 | 12/2001 | Burrell |
| 6,420,622 B1 | 7/2002 | Johnston |
| 6,461,467 B2 | 10/2002 | Blatchford |
| 6,472,581 B1 | 10/2002 | Muramatsu |
| 6,479,724 B1 | 11/2002 | Areskoug |
| 6,552,244 B1 | 4/2003 | Jacques et al. |
| 6,559,351 B1 | 5/2003 | Eakin |
| 6,566,575 B1 | 5/2003 | Stickels et al. |
| 6,566,576 B1 | 5/2003 | Komerska et al. |
| 6,566,577 B1 | 5/2003 | Addison |
| 6,600,085 B2 | 7/2003 | Sun et al. |
| 6,610,411 B2 | 8/2003 | Daoud et al. |
| 6,649,804 B2 | 11/2003 | Eakin |
| 6,653,520 B1 | 11/2003 | Mouton |
| 7,119,247 B2 | 10/2006 | Worthley |
| 2002/0082539 A1 | 6/2002 | Battah et al. |
| 2002/0107466 A1 | 8/2002 | Faasse, Jr. |
| 2002/0156410 A1 | 10/2002 | Lawry |
| 2002/0193723 A1 | 12/2002 | Batdorf |
| 2003/0040691 A1 | 2/2003 | Griesbach, III et al. |
| 2003/0059626 A1 | 3/2003 | Daoud |
| 2003/0088202 A1 | 5/2003 | Gilman |
| 2003/0120229 A1 | 6/2003 | de Jong et al. |
| 2003/0125654 A1 | 7/2003 | Malik |
| 2003/0167028 A1 | 9/2003 | Binder et al. |
| 2003/0194526 A1 | 10/2003 | Vesley et al. |
| 2003/0199800 A1 | 10/2003 | Levin |
| 2003/0204159 A1 | 10/2003 | Lawry |
| 2004/0133143 A1 | 7/2004 | Burton et al. |

FOREIGN PATENT DOCUMENTS

| | | |
|---|---|---|
| EP | 0160572 | 11/1985 |
| EP | 0106440 | 11/1987 |
| EP | 0413251 | 11/1994 |
| EP | 0799693 A2 | 10/1997 |
| EP | 1374813 A2 | 1/2004 |
| GB | 898826 | 6/1962 |
| JP | 05069512 A | 3/1993 |
| WO | WO89/08555 | 9/1989 |
| WO | WO02062403 A1 | 8/2002 |
| WO | WO03026544 A1 | 4/2003 |
| WO | WO03043553 A1 | 5/2003 |
| WO | WO03045294 A1 | 6/2003 |
| WO | WO03055536 A1 | 7/2003 |
| WO | WO03057103 A1 | 7/2003 |
| WO | WO03061538 A1 | 7/2003 |
| WO | WO03061539 A1 | 7/2003 |
| WO | WO03068283 A2 | 8/2003 |
| WO | WO03086255 A1 | 10/2003 |

OTHER PUBLICATIONS

Smith & Nephew—Cutinova Hydro downloaded on Apr. 29, 2004 at http://wound.smith-nephew.com/us/Standard.asp?Nodeld=2608.

Krieser, Jason, K., et al., "Comparison of Hydrophilic Polyurethane Foam Dressings", downloaded on Jun. 16, 2003, at http://woundcare.org/newsvol2n2/pr12.htm.

Moist Wound Healing, downloaded Jun. 16, 2003 at http://www.lawrenceville.org/mgolden/moistwd.html.

Molnlycke Health Care's Business Area Wound Care Global, Safetac technology, Silicone. (2004).

Molnlycke Health Care's Business Area Wound Care Global, Safetac technology, Safetac technology. (2004).

Molnlycke Health Care's Business Area Wound Care Global, Mepilex. (2004).

Thomas, Steve, Ph.D., "Soft silicone dressings: frequently asked questions", World Wide Wounds, www.worldwidewounds.com/2003/october/Thomas/Soft-Silicone-FAQ.html.

Tendra Open Wound Care System, Tendra Mepilex Transfer. Product brochure (2004).

Ulman, Katherine L., et al. "Silicone Pressure Sensitive Adhesives for Healthcare Application", p. 724-747.

Thomas, David R., MD. "Prevention and treatment of pressure ulcers: What works? What doesn't?", Cleveland Clinic Journal of Medicine, vol. 68, No. 8, Aug. 2001, pp. 704-722.

Thomas, Steve, Ph.D., "Atraumatic dressings", World Wide Wounds, www.worldwidewounds.com/2003/january/thomas/atraumatic-dressings.html.

Tendra Open Wound Care System, Mepilex Border, product brochure (2004).

Versiva, "Innovative Moisture Management", downloaded Jan. 16, 2004 at http://www.convatec.com/versiva/us/three_proven_tech.htm.

Smith & Nephew—Allevyn Adhesive, downloaded Jan. 16, 2004 at http://wound.smith-nephew.com/us/Product.asp?NodeID=452&UniqueID=0.9.393 . . . .

Smith & Nephew—Allevyn Technology, downloaded Jan. 16, 2004 at http://wound.smith-nephew.com/us/Standard.asp?NodeID=2711&UniqueID=0.92594 . . . .

"Silicone Gel Breast Implants", The Report of the Independent Review Group, What is Silicone?; downloaded on Jan. 27, 2005 at http://www.silicone-review.gov.uk/silicone/index.htm.

"Silicone Chemistry Overview", pp. 1-12, 1997, Down Corning Corporation.

Bentley, David, "A Primer on How to Put Substrates Together", Paper, Film & Foil Converters, downloaded on Jan. 27, 2005 at http://pffc-online.com/unprinted_rolls/paper_coatinglaminaging/.

Technical Data Sheet, inspire 6200, 30 μm Polyurethane Film with Hydrogel PSA, 2001-2002.

Technical Data, Platilon H, Thermoplastic Adhesive Films, epurex films, BayerMaterialSecience.

* cited by examiner

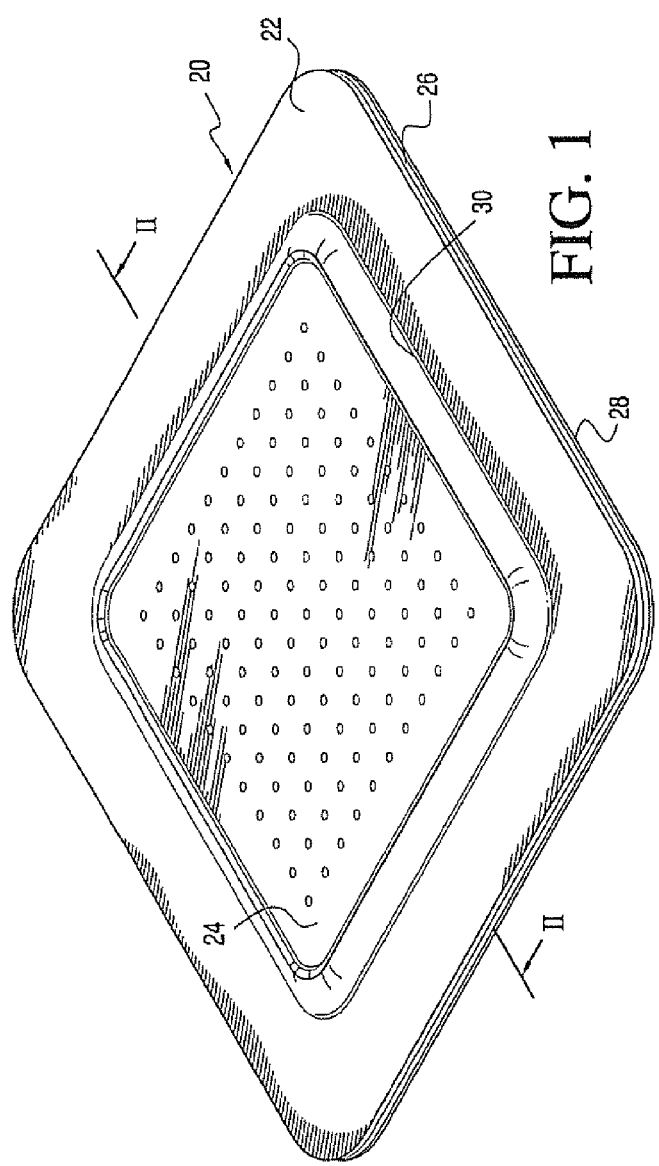
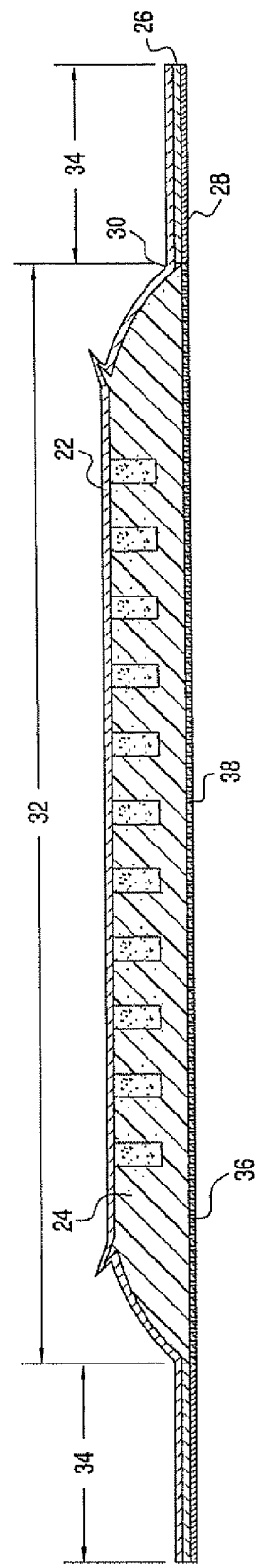
FIG. 1
FIG. 2

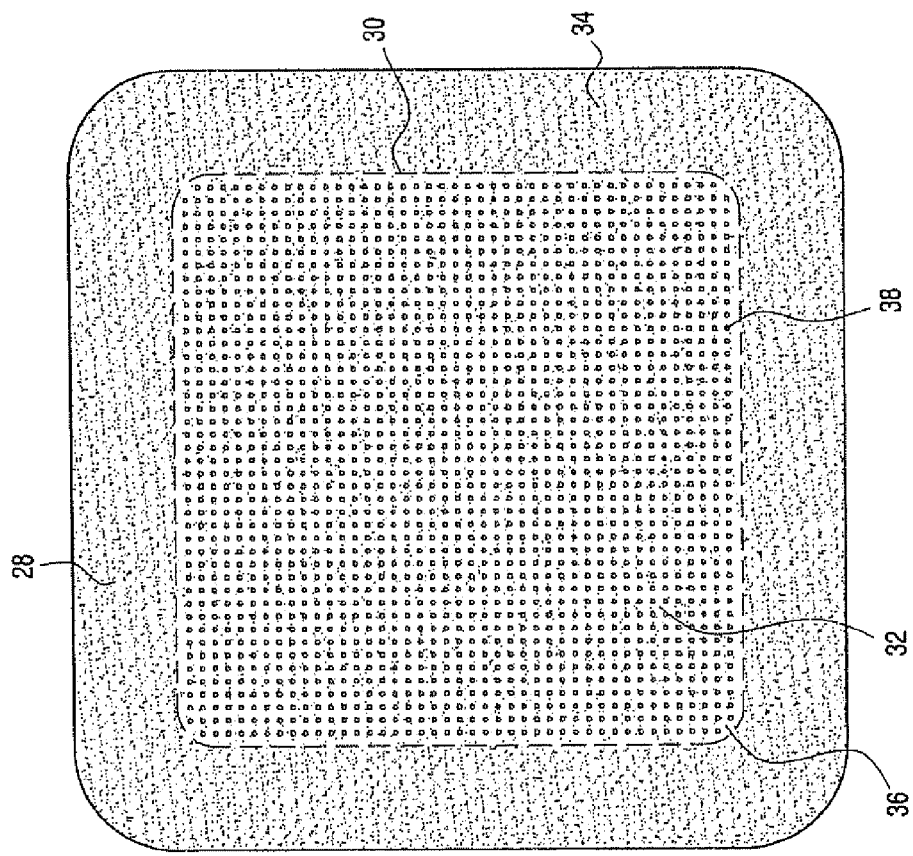
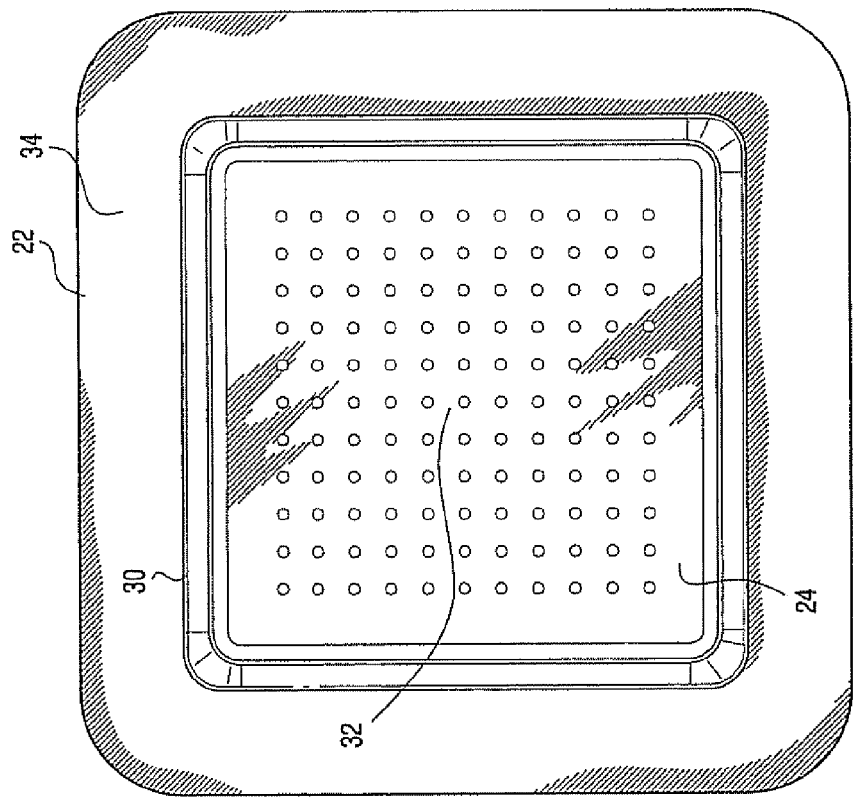
FIG. 3
FIG. 4

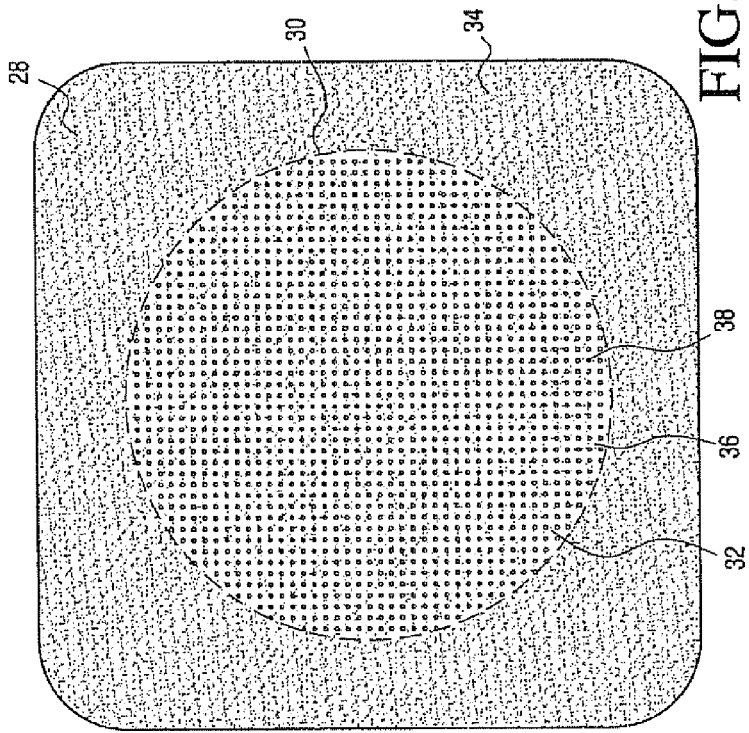
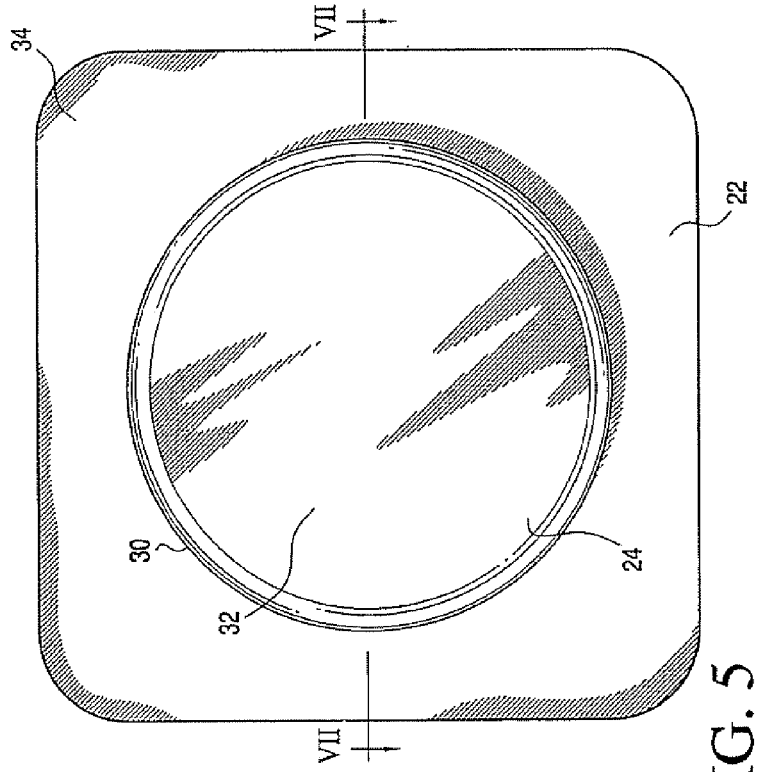
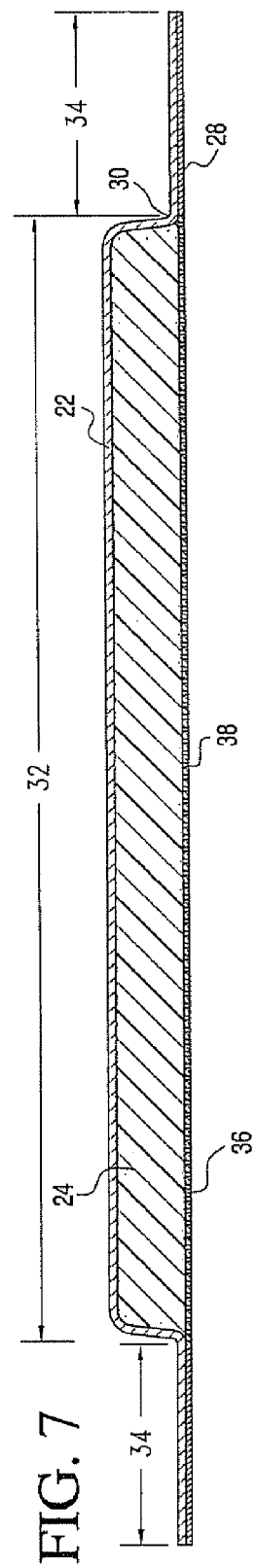
FIG. 5
FIG. 6
FIG. 7

WOUND DRESSING AND METHOD FOR MANUFACTURING THE SAME

CROSS REFERENCE TO RELATED APPLICATIONS

This application is a continuation of U.S. application Ser. No. 11/136,465 filed on 25 May 2005 which is a continuation-in-part of application Ser. No. 10/924,861 filed 25 Aug. 2004, now U.S. Pat. No. 7,396,975, claiming the benefit of U.S. provisional application Nos. 60/503,546 filed 17 Sep. 2003, 60/518,317 filed 10 Nov. 2003, and 60/543,401 filed 11 Feb. 2004.

BACKGROUND

Historically, many diverse materials of various origins have been used to treat wounds by absorbing wound fluids and tissue ("exudate") from a wound site with an absorbent material. In recent years, use of polymeric-based wound care products have become increasingly popular to control wound site environmental factors such as water vapor, oxygen permeability, bacterial impermeability, and absorption of exudate. Such wound care products are tailored to meet specific requirements including conformability to a body portion, selective adherence to a wound bed, and adhesiveness to the skin surrounding the wound site.

Recently, occlusive or moisture-retentive dressings have gained increasing acceptance in treating wounds, in particular pressure sores and ulcers. A wide variety of wound care products are known in the art for receiving, absorbing, and retaining exudate. Typically, these wound care products include polymeric foams, polymeric films, particulate and fibrous polymers, hydrogels, and hydrocolloids. Dressings with at least one of these components promote wound healing by providing a moist environment, while removing excess exudate and toxic components, and further serve as a barrier to protect the wound from secondary bacterial infection. While these known wound dressings can effectively manage a wound, many have been found to possess certain limitations or disadvantages.

Developments in the field of silicone manufacturing have led Össur hf of Reykjavik, Iceland, and assignee of the present invention, to produce silicone products adapted for skin contact that provide superb softness, and gentle skin contact. In particular, such silicone manufacturing has led to advances in improved comfort and cushioning of prosthetic suspension liners that have excellent durability and intimacy using proprietary silicone technology of Össur hf. It has been found that by applying the silicone technology of Össur hf, a silicone adhesive layer can be produced that possesses superior gentle adherence to wound sites while not damaging skin and the wound bed.

While a wound dressing having a silicone adhesive layer provides gentle adhesion to the wound and the surrounding skin, there are many instances where it is required that the wound dressing has greater tackiness in outer lying regions bordering the wound. Difficulties arise in that there must be a balance of gentle adhesion at the wound site and adjacent areas of skin so as to avoid disrupting the wound, while still providing sufficient adhesion of the dressing to accommodate movement of a patient.

For the foregoing reasons, there is a demand for an improved wound dressing that reduces wound trauma upon wound dressing changes, improves the durability and lifetime of the wound dressing, anatomically conforms to a wound, possesses improved fluid uptake, retention and removal properties, and can be securely maintained on a patient's body. It is thus desired to produce a wound dressing having an adhesive layer that does not possess the drawbacks of known adhesive layers, and instead, gently adheres and detaches from a wound site while providing superior fluid uptake. Moreover, there is a demand for a wound dressing that includes adhesive means having greater skin adherence than an adhesive layer disposed over a wound.

SUMMARY

The present invention is directed to an improved wound dressing possessing superior skin adherence capabilities.

In accordance with a first embodiment, a wound dressing includes a vapor-permeable backing layer defining first and second surfaces, and a center portion and a border portion bordering the center portion. A first skin-adherent facing layer connects to the border portion along the first surface of the backing layer. An absorbent core is also provided which has first and second surfaces. The second surface of the absorbent core is secured to the first surface of the backing layer generally within the boundaries of the center portion of the backing layer. The second surface of the absorbent core forms a portion of a proximal surface of the wound dressing and is non-adherent to skin.

In a second embodiment, a wound dressing includes the backing layer and first facing layer described above in reference to the first embodiment. Additionally, an absorbent core is provided which has first and second surfaces, and is connected to the center portion of the first surface of the backing layer. A second skin adherent facing layer is disposed along the first surface of the absorbent core and is a pressure sensitive adhesive.

According to a third embodiment, a wound dressing similarly includes the backing layer, first facing layer and absorbent core of the second embodiment. Furthermore, this embodiment includes a perforated covering layer having first and second surfaces of which the first surface is secured to the second surface of the absorbent core. The covering layer is generally non-adherent to skin.

In a fourth embodiment, a wound dressing similarly includes the backing layer, first facing layer and absorbent core of the second embodiment. Moreover, a perforated silicone sheet is provided having first and second surfaces wherein the first surface is adjacent to the second surface of the absorbent core. The silicone sheet has at least one surface that is generally non-tacky.

In a fifth embodiment, a wound dressing is provided having a center portion that defines a perimeter having a shape that does not correspond to a perimeter shape of the border portion. According to one variation, the shape of the absorbent core corresponding to the center portion is generally circular while the perimeter shape of the border portion is generally square or rectangular. This embodiment may include any of the features described in reference to the other embodiments described in this section.

BRIEF DESCRIPTION OF THE DRAWINGS

Pursuant to the description that follows, each of the aforementioned embodiments includes variations and combinations that will become better understood with regard to the following description, appended claims, and accompanying drawings where:

FIG. 1 is perspective view showing an embodiment of a wound dressing according to the invention;

FIG. 2 is a sectional view of the embodiment of FIG. 1 taken along line II-II;

FIG. 3 is a top plan view of the embodiment of FIG. 1;

FIG. 4 is a bottom plan view of the embodiment of FIG. 1;

FIG. 5 is a top plan view of another embodiment of the wound dressing;

FIG. 6 is a bottom plan view of the embodiment of FIG. 5;

FIG. 7 is a sectional view of the embodiment of FIG. 5 taken along line VII-VII;

DETAILED DESCRIPTION OF VARIOUS EMBODIMENTS

Overview

Figure 8:
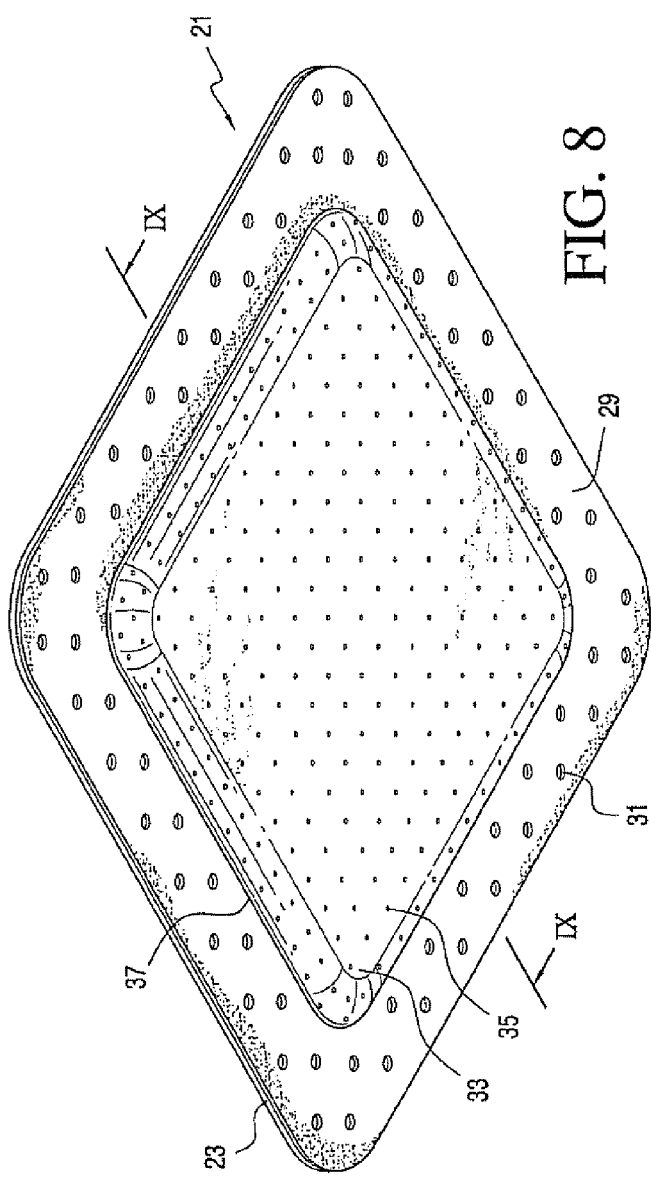
FIG. 8 is a bottom perspective view of another embodiment of the wound dressing.

A better understanding of different embodiments of the invention may be had from the following description read in conjunction with the accompanying drawings in which like reference characters refer to like elements.

While the disclosure is susceptible to various modifications and alternative constructions, certain illustrative embodiments thereof are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for"performing a specified function, or "step for" performing a specific function, is not to be interpreted as a "means" or "step" clause as specified in 35 U.S.C. §112, paragraph 6.

Environment and Context of Embodiments

Various embodiments of the invention are provided to variously be used to absorb exudate, combat odor and infection, relieve pain, wound cleanse and maintain a moist environment at a wound surface to facilitate healing of the wound. The embodiments of the invention are particularly configured to absorb exudate or wound fluid and may therefore be suitable for application for a variety of different wound types.

The various embodiments are conformable to a variety of locations on a living body, and may be dimensioned to accommodate different types and sizes of wounds. Moreover, the adhesive properties may be modified according to the location and type of wound to be treated while taking into consideration the potential for the dressing to cause sensitivity reactions, the ease of application and removal including the production of pain and trauma to wound surfaces, and the interval between wound dressing changes.

Thus, it is to be clearly understood that the various embodiments of the wound dressing according to invention may be made in any desired sizes and shapes for use over any afflicted portion of a human or other living body.

While features are shown in the drawing figures that are not described in detail in the description that follows, a detailed description of such features may be found in application Ser. No. 10/725,574 that is incorporated herein by reference.

Various Embodiments of the Wound Dressing

As shown in FIG. 1, an embodiment of a wound dressing 20 includes a liquid impervious, vapor permeable backing layer 22 having proximal (first) and distal (second) surfaces. The backing layer 22 defines a center portion 32, and a border portion 34 surrounding the center portion 32. A carrier layer 26 is provided which has proximal and distal surfaces wherein the distal surface of the carrier layer 26 is secured to the proximal surface of the border portion 34 of the backing layer 22 and borders the center portion 32. A first skin adherent facing layer 28 is secured to the proximal side of the carrier layer 26.

The carrier layer 26 defines an opening corresponding to the center portion 32 of the backing layer 22, and substantially outlines the border portion 34.

As exemplified in FIGS. 2 and 3, an absorbent core 24 is secured to the proximal surface of the center portion 32 of the backing layer 22. The absorbent core 24 is positioned on the backing layer 22 such that the absorbent core 24 extends through the opening of the carrier layer 26. A second skin adherent facing layer 36 is disposed along a proximal surface of the absorbent core 24. According to this embodiment, the first facing layer 28 has greater skin adherence properties than the second facing layer 36.

In the embodiment shown in FIGS. 1-4, the backing layer 22 is thermal bonded to the carrier layer 26, and at least portions of the backing layer 22 are secured to the distal surface of the absorbent core 24. Moreover, the backing layer 22 may be thermal bonded to the absorbent core 24 at a boundary region 30 near or at the peripheral edges of the proximal surface thereof. By thermal bonding the absorbent core 24 to the backing layer 22, a seal may be formed along the regions of bonding. A bevel may also be defined near the peripheral edges of the absorbent core to gradually reduce stresses of the absorbent core as it absorbs wound exudate and to minimize imprints on skin of a wearer.

It will be pointed out that the backing layer may be secured to the carrier layer and the absorbent core in any manner known to one skilled in the art of wound dressings, and any such methods are within the scope of this application. Such other methods include using an adhesive, thermo bonding, pressure molding, or mechanical fixation with elements such as stitches, pins or staples.

Preferably, the first facing layer 28 is a silicone gel coated onto the carrier layer 26, and the second facing layer 36 is a discrete sheet of silicone gel directly secured to the absorbent core 24. As shown more fully in FIG. 4, the second facing layer 36 includes a plurality of apertures 38 that are preferably arranged in a predetermined pattern such that they are equally spaced from one another and possess a generally uniform size and shape.

While the first facing layer 28 is shown in FIG. 4 as not including apertures, the first facing layer 28 may be configured to include a plurality of apertures in a similar formation as those described above in reference to the second facing layer 36. Furthermore, alternative embodiments regarding the pattern, configuration and dimension of the apertures of the facing layers is provided in application Ser. No. 10/725,574.

As illustrated in FIGS. 5-7, in a variation of the wound dressing of FIG. 1, the perimeter of the center portion 32 has a shape that is different from the shape of the perimeter of the border portion 34. This is particularly exemplified by the generally circular-shaped absorbent core 24, and the border portion 34 generally defining a square-shaped perimeter. According to this embodiment, the first facing layer 28 is secured directly to the backing layer 22, and the second facing layer 36 defines a plurality of apertures 38. Moreover, the transition 30 between the center and border portions is generally defined as a linear drop.

In yet further variations, the border and center portions may comprise a variety differently shaped perimeters including but not limited to. These shapes may be determined on the basis of an intended wound bed shape, and their efficacy for treating such a wound bed.

Figure 9:
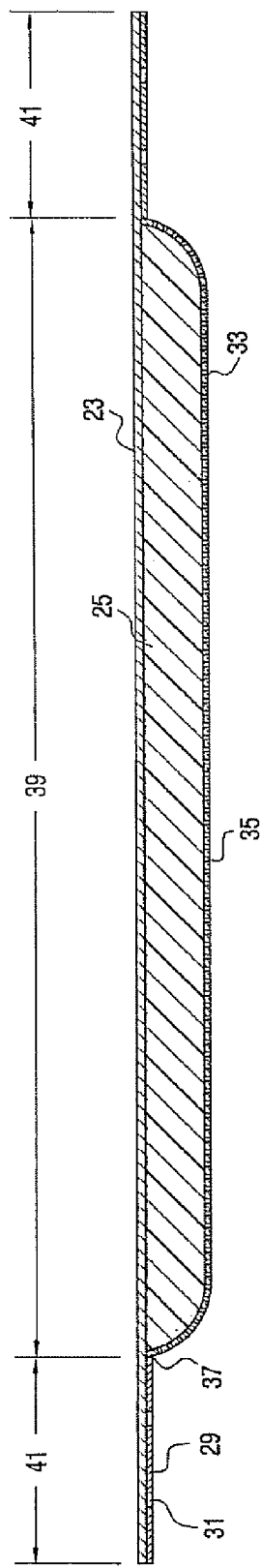
FIG. 9 is a sectional view of the embodiment of FIG. 8 taken along line IX-IX.

FIGS. 8 and 9 show another embodiment of the wound dressing including a backing layer 23 having proximal and distal surfaces. The backing layer defines a center portion 39 and a border portion 41 surrounding the center portion 39. A first skin adherent facing layer 29 is secured to the proximal surface of the backing layer 23. The first facing layer 29 defines a plurality of apertures 31.

A substantially planar distal surface of an absorbent core 25 is secured to the proximal surface of the center portion 39 of the backing layer 23. A second skin adherent facing layer 33 is secured to a proximal surface of the absorbent core 25. The second facing layer 33 defines a plurality of apertures 35 arranged in a pattern. A boundary 37 delimits the first and second facing layers 29, 31, and distinguishes the center and border portions 39, 41 of the dressing.

Figure 10:
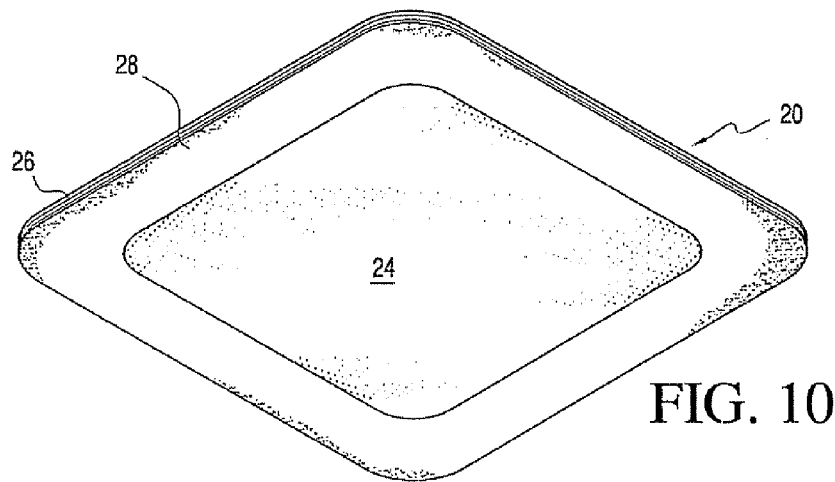
FIG. 10 is a bottom perspective view of another embodiment of the wound dressing.
Figure 11:
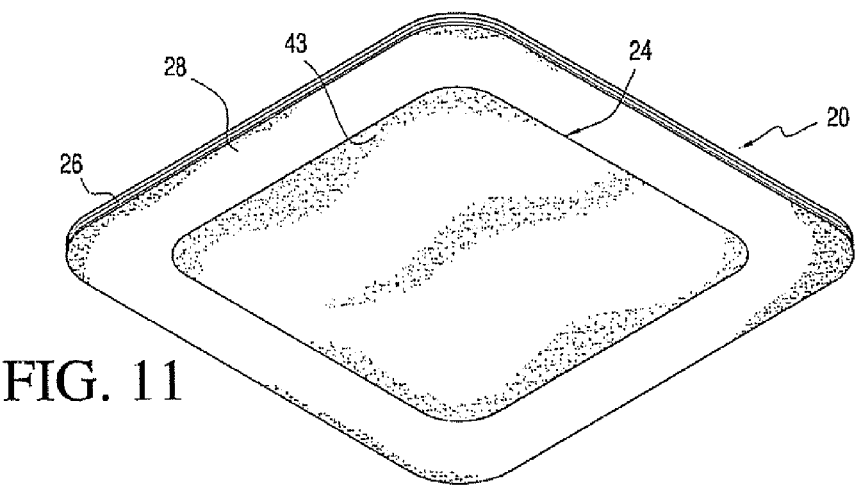
FIG. 11 is a bottom perspective view of yet another embodiment of the wound dressing.
Figure 12:
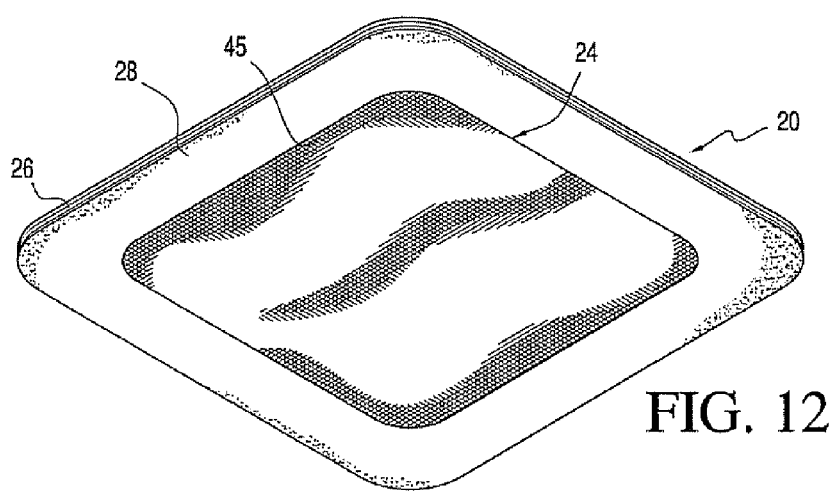
FIG. 12 is a bottom perspective view of yet another embodiment of the wound dressing.

FIGS. 10-12 show variations of the embodiment of the wound dressing according to FIGS. 1-4, however each of these variation are either without a second facing layer or have a second facing different from the second facing layer according to the embodiment of FIGS. 1-4.

Specifically, FIG. 10 shows a wound dressing with the absorbent core 24 having an exposed absorbent core surface that is intended to lie proximal against the skin or a wound site. As will be discussed later, the absorbent core may comprise a variety of different materials and combinations thereof. According to this embodiment, the absorbent core is preferably hydrophilic foam.

It will be noted that non-hydrophilic foams may be used in accordance with this embodiment. For example, silicone foam may be used that is formed by conventional methods and using materials such as those described in U.S. Patent Application Publication 2002/0193723, and incorporated herein by reference.

The absorbent core 24 may be constructed in a manner such that the surface which lies proximal to skin is non-adherent. For example, the absorbent core may comprise at least two layers of foams having different densities as described in U.S. Pat. No. 5,632,731, and incorporated herein by references. In yet another variation, the absorbent core may be constructed from foam which has some skin adherent properties.

FIG. 11 illustrates another embodiment of a wound dressing wherein the center portion of the absorbent core 24 is directly coated with an adhesive 43. According to this embodiment, the adhesive is an acrylic pressure sensitive adhesive.

The adhesive layer 43 may comprise various pressure sensitive adhesives to render the center proximal portion of the absorbent core 24 tacky to the skin. The pressure sensitive adhesive is preferably reasonably skin compatible and hypoallergenic.

The adhesive may be formed from one or more adhesive materials selected from the group consisting of acrylic copolymer, polyisobutylene, polyurethane and polymeric silicone. The adhesive layer 43 may also comprise two or more adhesive materials in a stacked arrangement, or may be different adhesive materials arranged in alternating parallel strips to one another. The adhesive is substantially impermeable to liquid water, but preferably has a moisture vapor transmission rate greater than about 100 g/m 2/24 hr. In a variation, however, the adhesive may be a hydrogel suitable for use in a wound dressing environment.

FIG. 12 shows another embodiment wherein the center portion of the absorbent core 24 is covered along its proximal side with a perforate covering layer 45. The layer 45 may be flexible, and be formed from a woven or non-woven material, polymeric mesh or net, or a perforated film formed from a polymeric material. The layer 45 may be non-adherent to the skin or a wound site, and may be secured to the absorbent core with an adhesive or be laminated onto the absorbent core. In addition to the perforated structure, the material of layer 45 may be selected to allow for moisture evaporation therethrough.

According to this embodiment, the layer 45 is perforated in a generally uniform manner. In variations, the layer may be perforated in different arrangements such as in the variations of the silicone facing layer described in application Ser. No. 10/725,574.

In a variation of this embodiment, the layer may comprise a perforated silicone sheet. Such silicone sheet may include a first side that is tacky and another side that is substantially non-tacky. In further variations, both sides of the silicone sheet may be tacky, or non-tacky.

The silicone sheet may be formed from a cured silicone elastomer mixture, for example MED-4905 manufactured by NuSil Technology (Carpenteria, Calif.). When curing the silicone mixture, the silicone sheet is cured on a perforation plate, such as one of those described in application Ser. No. 10/725,574, so as to form a plurality of apertures in the silicone sheet. At least one side of the silicone sheet is treated with a talcum powder or similar substance to mitigate or minimize the tackiness of such side. The silicone sheet is preferably free-standing and sufficiently durable for connecting to the second surface of the absorbent core.

Depending on the application of the wound dressing, either the tacky side or the non-tacky side of the silicone sheet may connect to the absorbent core. The silicone sheet may be applied to the absorbent core by placing the tacky side of the sheet along the second side of the absorbent core or, alternatively, the non-tacky side may be laminated or adhered to the second side of the absorbent core by known methods or those described in application Ser. No. 10/725,574. In addition, the silicone sheet may simply be applied to the wound site and the wound dressing is placed thereover.

The silicone sheet may be sufficiently durable and thick to be free-standing thereby permitting handling without its destruction. In such a configuration, the silicone sheet has a minimum thickness of 0.25 mm.

In a variation of the embodiments of FIGS. 11 and 12, the covering layer may be coated with the aforementioned pressure sensitive adhesive in connection with the embodiment of FIG. 11. According to this variation, the covering layer serves a similar function as the carrier layer disposed between the first facing layer and the backing layer in the embodiment of FIG. 1. The covering layer may be formed from a material similar to the carrier layer. On the other hand, for particular applications, materials such as PET or polypropylene in a sheet-like form may be used as the reinforcement layer. Alternatively, the reinforcement layer may be a "double-sided tape" comprising a substrate material coated on both surfaces with one or more of the adhesives described above.

While each of the embodiments related to FIGS. 10-12 show the first facing layer 28 as being generally imperforate, each these embodiments may be combined with the embodiment of FIG. 8 wherein the first facing layer has a plurality of apertures.

In another variation of the embodiment of FIG. 12, the carrier layer may extend across both of the center and border portions such that the same sheet comprises both the carrier layer and the covering layer. Of course, it is necessary that the center portion of the carrier layer have a plurality of perforations to permit the transport of exudate from the wound to the absorbent core. This variation may be configured in combination with a pressure sensitive adhesive that is deposited across the center portion of the absorbent core of the wound dressing. In other variations, the center portion of the carrier layer may have any one of the configuration of the first facing layer with the carrier layer in accordance with the embodiments of FIGS. 1-4 and 8-9.

Figure 13:
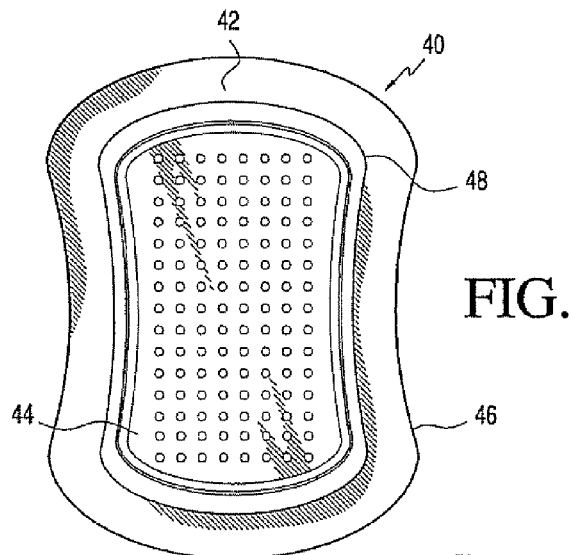
FIG. 13 is a top plan view of an embodiment having contoured peripheral edges of the wound dressing.
Figure 14:
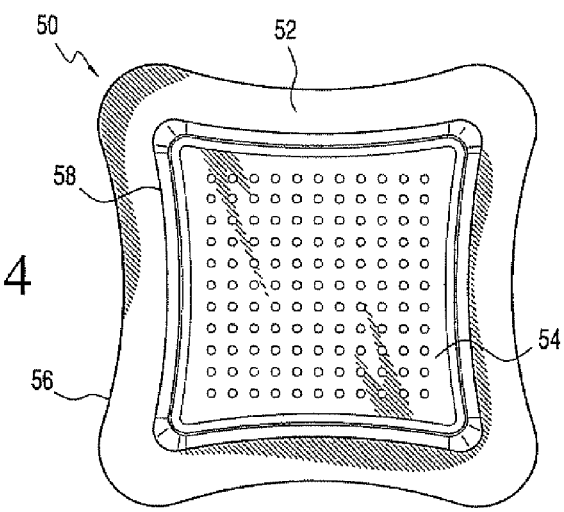
FIG. 14 is a top plan view of another embodiment having contoured peripheral edges of the wound dressing.
Figure 15:
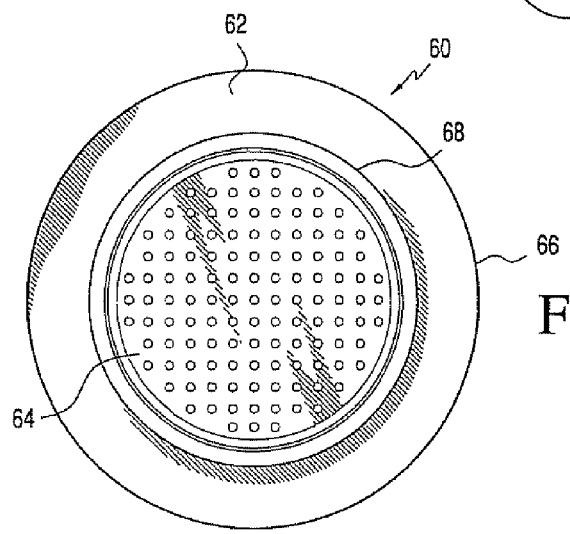
FIG. 15 is a top plan view of yet another embodiment having contoured peripheral edges of the wound dressing.

In addition to the basic footprint or configuration of the wound dressing exemplified in FIGS. 1-4, other configurations are possible and are fully within the scope of the present invention. FIGS. 13-15 show exemplary wound dressing embodiments generally having the same backing layer and absorbent core relationship as in the wound dressing of one any of the aforementioned embodiments. While each of the embodiments of FIGS. 13-15, the backing layer defines contoured outer edges and the absorbent core has contoured outer edges generally corresponding in shape to the contoured outer edges of the backing layer, any of these embodiments may have a relationship similar to the one described in connection with the embodiment of FIGS. 5-7.

FIG. 13 illustrates a dressing 40 having a backing layer 42 and an absorbent core 44 each with a generally elongate profile such that the outer edges 46, 48 of both the backing layer 42 and the absorbent core 44 are concave and convex at certain portions thereof. FIG. 14 shows another, embodiment of a dressing 50 wherein a backing layer 52 and an absorbent core 54 each have generally equal length outer sides 56, 58 that are both concave and convex. FIG. 15 shows yet another embodiment of a dressing 60 wherein the backing layer 62 and the absorbent core 64 have peripheral edges 66, 68 that are generally circular and concentric with one another.

Figure 16:
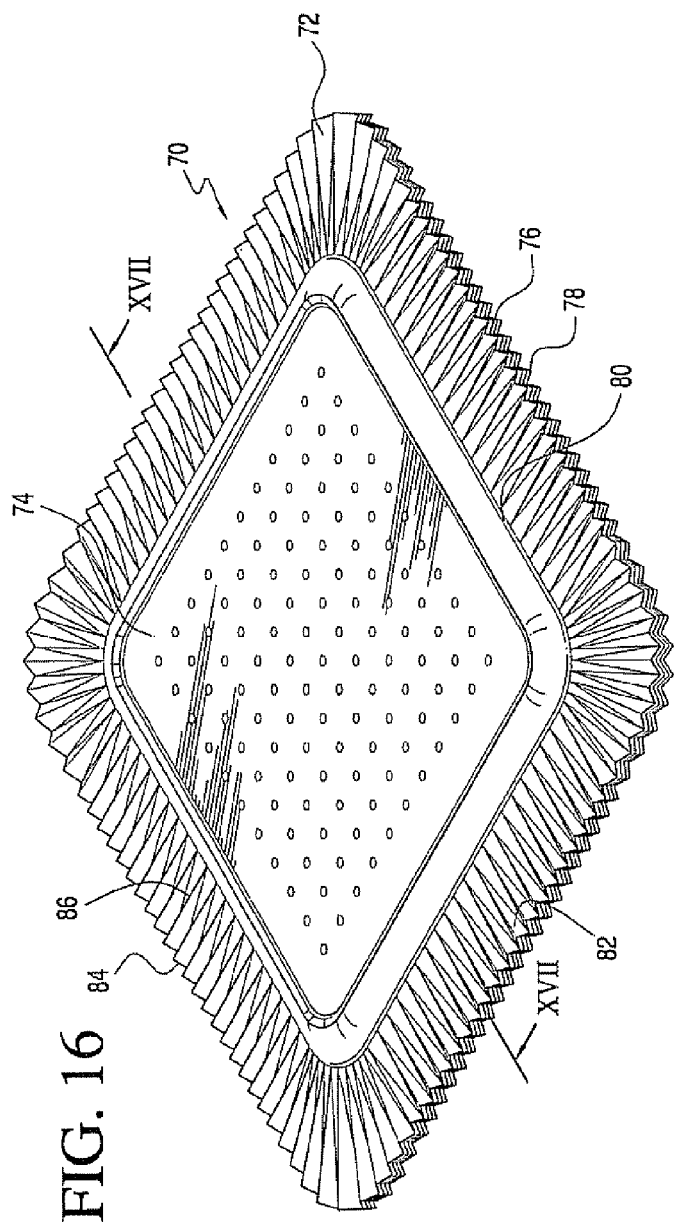
FIG. 16 is a perspective view of an embodiment having a pleated border portion of the wound dressing.
Figure 17:
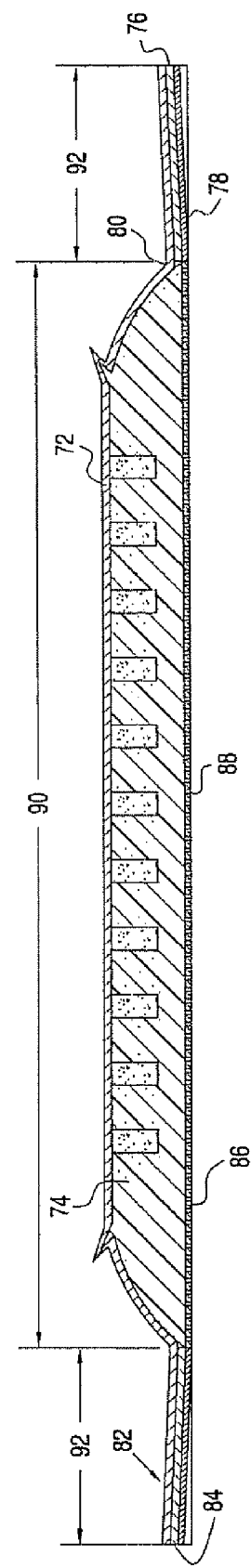
FIG. 17 is a sectional view of the embodiment of FIG. 16 taken along line XVII-XVII.

Turning to FIGS. 16 and 17, another embodiment of a wound dressing 70 is shown having a center portion 90 and a border portion 92. In the dressing 70, a proximal surface of a backing layer 72 is secured to a distal surface of an absorbent core 74 wherein a boundary 80 generally defined as the peripheral edges of the absorbent core 74 delimits the center portion 90 and border portion 92 of the dressing 70. A distal surface of a carrier layer 76 is secured to the proximal surface of the backing layer 72 and has an opening that generally surrounds the absorbent core 74, whereby the carrier layer 76 is associated with the border portion 92 and the absorbent core 74 is associated with the center portion 90 of the dressing 70. A first facing layer 78 is secured to the proximal surface of the carrier layer 76. A second facing layer 86 is secured to the proximal surface of the absorbent core 74 and defines a plurality of apertures 88.

In observing FIG. 17, the border portion 92 of the backing layer 72 defines a plurality of pleats 82 that extend from the peripheral edge 84 of the backing layer 72, and have a taper 86 that leads from the edge 84 towards the boundary 80. The pleats 82 are generally arranged around the border portion 92 of the dressing 70 and extend towards the center portion 90. The pleats 82 are equally formed by the carrier layer 76 and the first facing layer 78 as these layers generally follow the contours of the backing layer 72 within the border portion 92 thereof.

According to variations of this embodiment, the pleats may not include a taper and, moreover, the backing layer may comprise at least two discrete portions whereby each portion corresponds to a center portion and a border portion of the dressing. Such two backing layer portions may be joined at the boundary between the center and border portions of the dressing.

Figure 18:
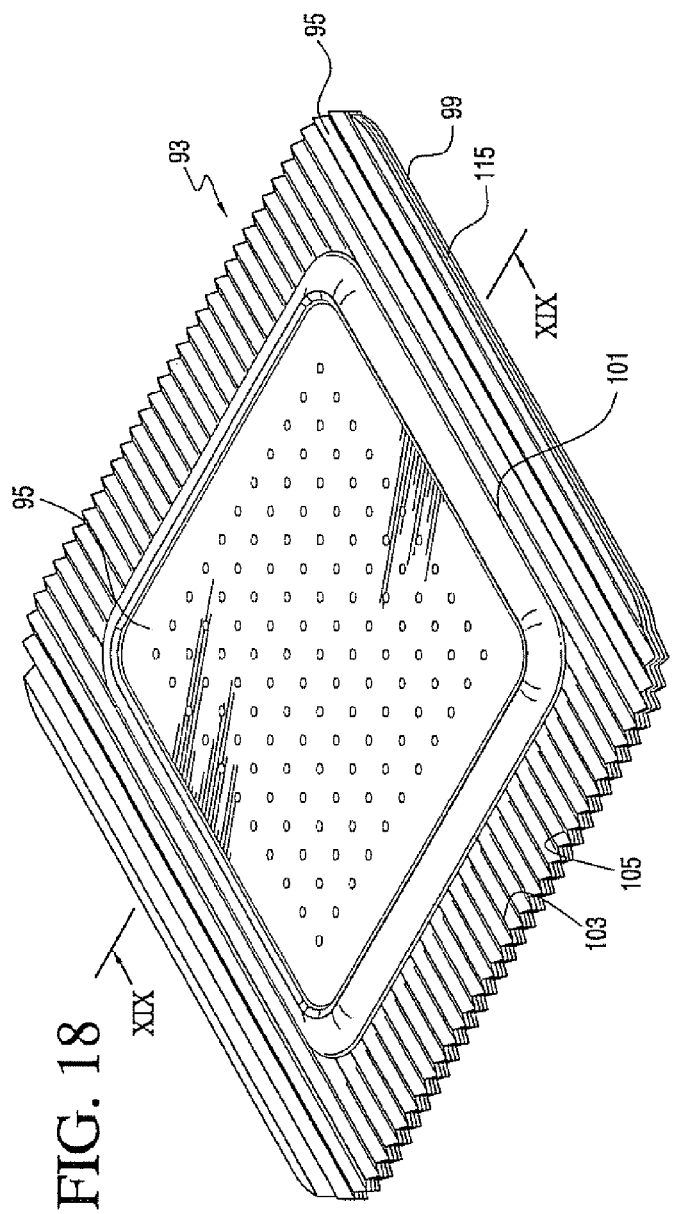
FIG. 18 is a perspective view of an embodiment having a border portion having an undulating profile of the wound dressing.
Figure 19:
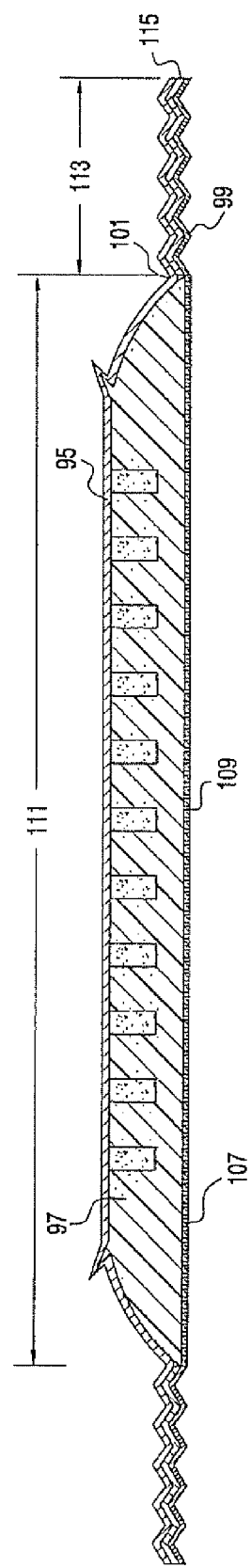
FIG. 19 is a sectional view of the embodiment of FIG. 15 taken along line XIX-XIX.

As illustrated in FIGS. 18 and 19, another embodiment of a wound dressing 93 is shown having a center portion 111 and a border portion 113. In the dressing 93, a proximal surface of a backing layer 95 is secured to a distal surface of an absorbent core 97 wherein a boundary 101 generally defined as the peripheral edges of the absorbent core 97 delimits the center and border portions 111, 113 of the dressing 93. A distal surface of a carrier layer 97 is secured to the proximal surface of the backing layer 95 and has an opening that generally surrounds the absorbent core 95, whereby the carrier layer 97 is associated with the border portion 113 and the absorbent core 97 is associated with the center portion 111 of the dressing 93. A first facing layer 99 is secured to the proximal surface of the carrier layer 95. A second facing layer 107 is secured to the proximal surface of the absorbent core 97 and defines a plurality of apertures 109.

In observing FIG. 19, the border portion 113 of the backing layer 95 has an undulating profile comprising alternating ridges 103 and grooves 105 In this embodiment, the ridges 103 and grooves are generally in a parallel arrangement and laterally extend across the width of the dressing 93. The ridges 103 and grooves 105 are equally formed by the carrier layer 97 and the first facing layer 99, and these layers generally follow the contours of the backing layer 95 within the border portion 113 of the dressing 93.

According to variations of this embodiment, the undulating profile may extend across or in portions along the border and center portions of the dressing. Moreover, the pitch and depth of the ridges and grooves may be modified as deemed necessary to provide capabilities such as a desired stretchability of the dressing. Moreover, the cross-section of the ridges and grooves may also be modified as considered necessary to provide optimum stretchability, absorbency and skin adhesion.

Figure 20:
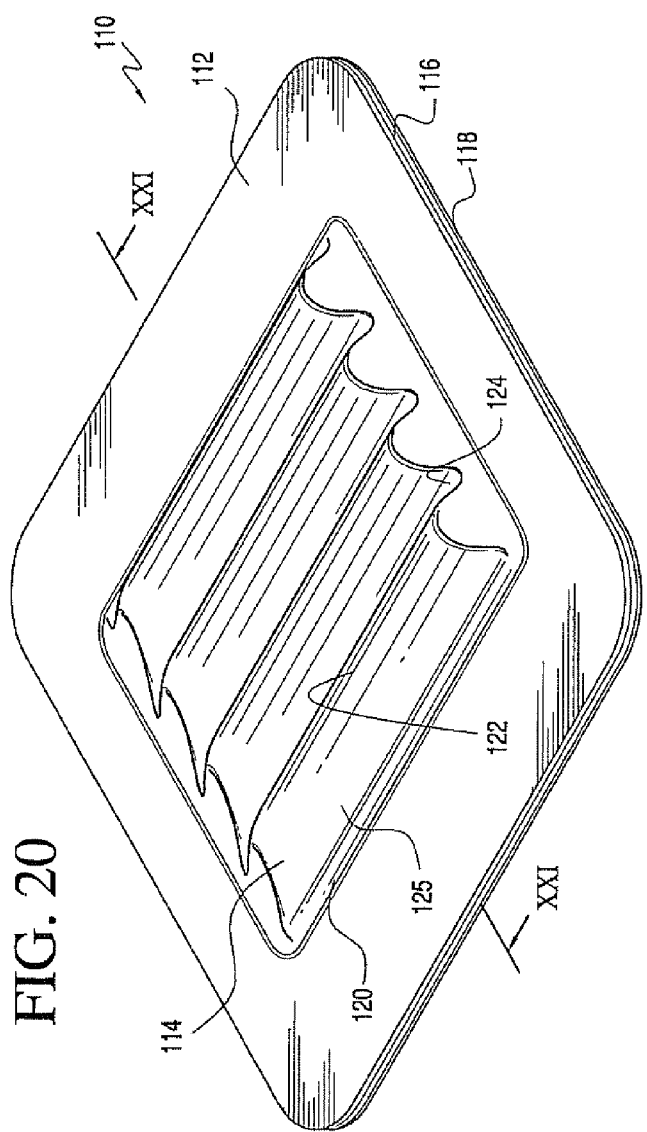
FIG. 20 is a perspective view of an embodiment with an absorbent core having an undulating profile of the wound dressing.
Figure 21:
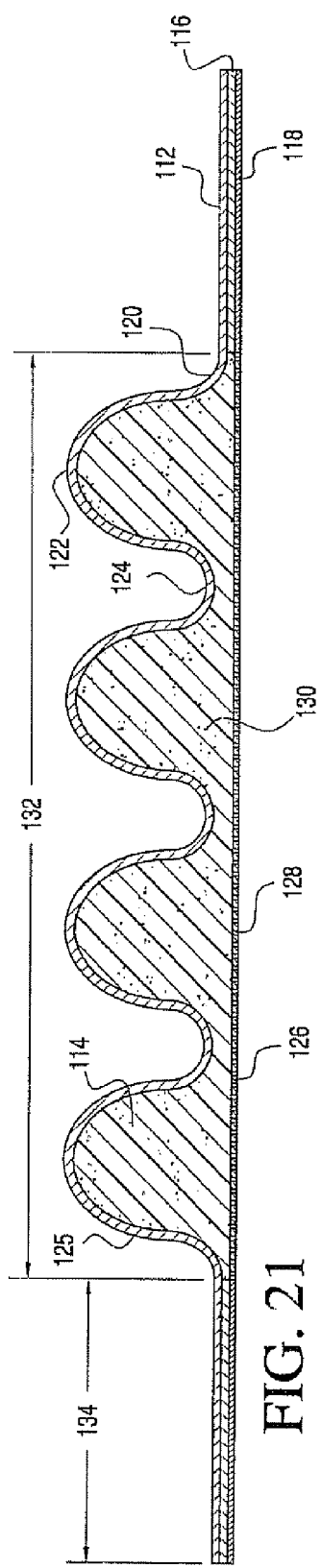
FIG. 21 is a sectional view of the embodiment of FIG. 17 taken along line XXI-XXI.

As illustrated in FIGS. 20 and 21, another embodiment of a wound dressing 110 is shown having a center portion 132 and a border portion 134. In the dressing 110, a proximal surface of a backing layer 112 is secured to a distal surface of an absorbent core 114 wherein a boundary 120 generally defined as the peripheral edges of the absorbent core 114 delimits the center and border portions 132, 134 of the dressing 110. A distal surface of a carrier layer 116 is secured to the proximal surface of the backing layer 112 and has an opening that generally surrounds the absorbent core 114, whereby the carrier layer 116 is associated with the border portion 134 and the absorbent core 114 is associated with the center portion 132 of the dressing 110. A first facing layer 118 is secured to the proximal surface of the carrier layer 116. A second facing layer 126 is secured to the proximal surface of the absorbent core 114 and defines a plurality of apertures 128.

In observing FIG. 21, the absorbent core 114 has an undulating profile comprising of alternating ridges 122 and grooves 124. In this embodiment, the ridges 122 and grooves 124 are generally in a parallel arrangement and laterally extend across the width of the absorbent core 114. As shown, the side portion 125 of the ridges 122 and grooves 124 is generally tapered to provide features such as greater conformability and absorption. The absorbent core 114 includes a plurality of hydrophilic particles 130 enmeshed therein, as explained in greater detail in application Ser. No. 10/725,574.

Variations of the embodiment shown in FIGS. 20 and 21 are possible in that the undulating profile may be modified according to a desirable configuration. For example, the ridges and grooves may be increased or decreased, and the cross-sectional profile of the ridges and grooves can be modified as considered necessary to provide features such as improved stretchability, absorbency and skin adherence.

Many of the facing layers used in the embodiments of the wound dressing of the present invention are preferably hydrophobic, such that they form liquid and moisture impervious layers. Moreover, these facing layers may be bonded to the proximal surface of the backing layer or carrier layer, or directly to the absorbent core.

In one of the preferred embodiments, the facing layers comprise a cross-linked silicone elastomer gel, such as, for example, a cross-linked silicone (polydimethyl siloxane gel) manufactured by NuSil Technology (Carpenteria, Calif.) under product designations MED-6340, or MED-6345 which is tackier than MED-6340. Preferably, the first facing layer comprises silicone gel under product designation MED-6345 and the second facing layer comprises silicone gel under product designation MED-6340.

According to the silicone based facing layers described herein, the method used to evaluate adhesion between the different facing layers includes measuring the force required to peel a 25 mm wide sample comprising a silicone gel layer from a stainless steel plate. The differences in the force (measured in N/25 mm) used to remove the sample indicate the difference in the skin adhesion. In the embodiments of the facing layers described herein, the adhesion level on stainless steel of the facing layers is as follows: border portion (first facing layer) is 1-3 N/25 mm and the center portion (second facing layer) is 0.0-1.0 N/25 mm.

As noted in connection to the embodiments of FIGS. 10-12, other facing layers may be used such as a pressure sensitive adhesive known to those skilled in the art of adhesives and wound dressings, and described in application Ser. No. 10/725,574. Moreover, the first facing layer may be provided with or without apertures, such as those defined by the second facing layer in each of the embodiments particularly described herein.

The silicone based facing layers preferably have a thickness within the range of 0.05 mm to 1.0 mm. The second facing layer is preferably 0.1 mm thick. The conformability of the dressing to the wound is somewhat dependent on thickness of the components, such that when the dressing is applied to a body portion, it conforms to the surface even when the surface is moved. The facing layers are arranged to stretch in order to accommodate the flexation of the joint but are preferably resilient to continue to conform to the surface when the surface is returned to its unflexed condition.

The various embodiments described herein using backing and carrier layers preferably comprise a thin polymeric elastic or flexible film coating providing a bacterial barrier formed from a water vapor permeable pliable elastomer material. The film is continuous in that it has no perforations or pores which extend through the thickness of the film. Films of this type are known and generally are hydrophilic polymeric materials through which water may diffuse.

The backing layer is connected to the distal surface of the absorbent core, and according to various embodiments, the backing layer is secured only to the distal surface and edges of the absorbent core, and does not penetrate any pores, cells or cavities of the absorbent core.

According to some embodiments, however, the carrier layer may possess a greater stiffness than the backing layer so as to provide greater control of applying the border portion of the dressing on skin and preventing curling, wrinkling or sticking of parts of the first facing layer to each other upon repeated application and removal of the dressing.

The backing layer may comprise polyurethane, such as a polyurethane film available from InteliCoat Technologies (South Hadley, Mass.) under product designation INSPIRE 2301, elastomeric polyester, blends of polyurethane and polyester, polyvinyl chloride, and polyether-amide block copolymer. The backing layer for use in the embodiments described herein is a polyurethane film since it exhibits a resilient property that allows the film to have good conformability and further has a high degree of stretchability.

The backing layer may be at least translucent, and more preferably, sufficiently transparent so that the wound site to which the dressing is applied can be viewed through the dressing. It is advantageous to view to evaluate the wound and healing thereof without removal of the dressing so as to avoid unnecessary handling of the dressing and exposure of the wound to the environment, and to reduce the likelihood of contamination.

Suitable continuous conformable backing layers have a moisture vapor transmission rate (MVTR) of the backing layer alone of 1500 to 14600 g/m^2/24 hrs, preferably 2500 to 2700 g/m^2/24 hrs at 38° C. The backing layer thickness is preferably in the range of 15 to 45 micrometers, more preferably 30 micrometers.

The preferred carrier layer is a thermoplastic elastomeric film that can be thermal bonded to the backing layer. An example of such a film is manufactured by Epurex films under the product designation Platilon U073. Alternatively, other films, foams and mesh substrates may be employed that can be thermal bonded to the backing layer, or secured to the backing layer by other methods including the use of adhesives, stitching, pins, and staples. Preferably, the carrier layer should be sufficiently stiff so as to reinforce the border portion of the backing layer.

Suitable continuous conformable carrier layers have a moisture vapor transmission rate (MVTR) of the carrier layer alone of 1,000 to 30,000 g/m^2/24 hrs, preferably 14,000 g/m^2/24 hrs at 38° C. The carrier layer thickness is preferably in the range of 45-100 micrometers, more preferably 60 micrometers.

The absorbent core may be selected from a variety of different types known within the art of wound dressings, and the construction thereof may be configured in a variety of different arrangements, as discussed more fully in application Ser. No. 10/725,574.

Figure 22:
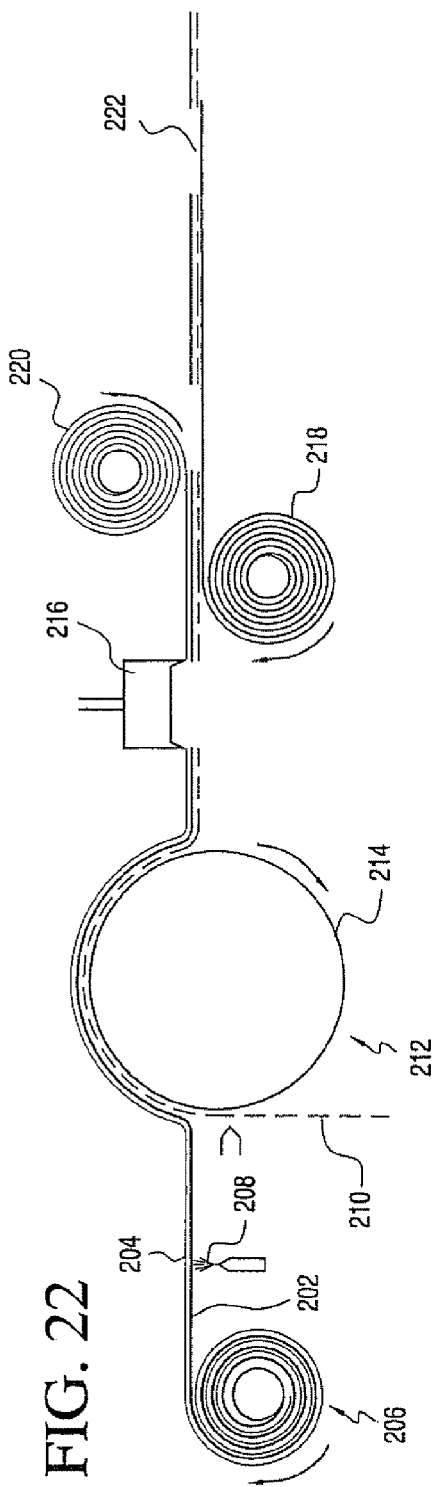
FIG. 22 is a schematic view showing a process for making features of the wound dressing.

Numerous methods of manufacturing may be employed to make the embodiments of the wound dressing described herein. According to one method exemplified in FIGS. 22 and 23, the method for manufacturing a wound dressing comprises the steps of providing a carrier layer 202 carried by a removable paper 204 and dispensed from a carrier layer roll 206. The carrier layer 202 is transported and a surface treatment substance 208 is applied on a proximal surface of the carrier layer 202. Preferably, the substance 208 is permitted to remain on the carrier layer 202 for approximately 30 minutes and maintained at 25° C. prior to the next step of the method to allow for any solvents in the primer to evaporate.

A suitable surface treatment substance includes silicone primers, such as those discussed more fully in application Ser. No. 10/725,574.

Next, a layer of an uncured silicone gel 210 is extruded onto the proximal surface of the carrier layer 202 over the substance 208. The carrier layer 202 with the uncured silicone gel layer 210 is transported over a drum 212 having a surface temperature of approximately 130° C. and maintained on the drum 212 for approximately 20 minutes. The drum 212 may be coated with any suitable release agent, such as Teflon, that will prevent adherence of the silicone gel 210 after curing thereof.

After the silicone gel layer 210 has cured and the carrier layer 202 is removed from the drum 212, a die cutter 216 is used to remove a center portion from the carrier layer 202. The removal of a center portion of the carrier layer 202 effectively forms an opening 222 through the carrier layer 202 and the cured silicone gel layer 210. Subsequently, the carrier layer paper 204 is removed from the distal surface of the carrier layer 202 onto a roll 220. A release paper or film 218 is applied to the proximal surface of the silicone gel layer 210.

The absorbent core 224 is inserted within the opening 222 of the carrier layer 202 and the layer of silicone gel 210. A second facing layer 226 is provided on a proximal surface of the absorbent core 224. The second facing layer 226 is preferably an apertured discrete layer of silicone gel. Methods for making the apertured second facing layer 226 are discussed more fully in application Ser. No. 10/725,574.

Figure 23:
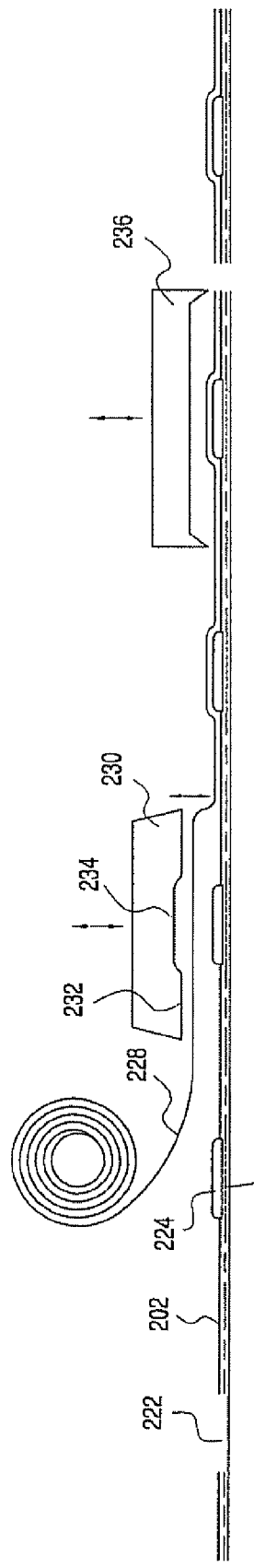
FIG. 23 is a schematic view showing a process for making features of the wound dressing.

According to the depiction in FIG. 23, a backing layer 228 is disposed over the distal surfaces of the carrier layer 202 and absorbent core 224. A platen 230 is provided as having a generally planar border region 232 and a recessed center region 234 relative to the planar border region 232 that generally corresponds to the shape of the absorbent core 224. The platen 230 is preferably heated to an elevated temperature suitable to thermal bond the backing layer 228 and the carrier layer 202 to one another and secure the absorbent core 224 thereon.

A backing layer 228 is disposed over the distal surfaces of the carrier layer 202 and absorbent core 224. A platen 230 is provided as having a generally planar border region 232 and a recessed center region 234 relative to the planar border region 232 that generally corresponds to the shape of the absorbent core 224. The platen 230 is preferably heated to an elevated temperature suitable to thermal bond the backing layer 228 and the carrier layer 202 to one another and secure the absorbent core 224 thereon.

The platen 230 is urged against the distal surface of the backing layer 228 to generate pressure thereon sufficient to substantially cause thermal bonding of the backing layer 228 to the carrier layer 202. After a period of time sufficient to thermal bond the backing layer 228 to the carrier layer 202 and to at least portions of the absorbent core 224, the platen 230 is removed from the distal surface of the backing layer 228.

Subsequent to the thermal bonding of the backing layer 228 to the carrier layer 202 and the absorbent core 224, the wound dressing is cut to size with a die cutter 236.

In variations of the described method, the platen 230 may be modified to impart the pleated or undulating profile of the embodiments of the wound dressing described herein. Alternatively, other platen systems may be used after the backing layer is secured to the carrier layer that has the pleated or undulating profiles. Such platen systems may include mutually opposed platens having the impression of the different bordered profiles described herein, and which are suitably heated to impart the aforementioned bordered profiles.

Suitable platens or die cutters may be employed that impart the undulating profile of the absorbent core described herein. Moreover, the undulating profile may be formed by methods including cutting the absorbent core, forming the absorbent core, and molding the absorbent core in the configuration described herein. Such configuration of the absorbent core is preferably achieved prior to the application of the backing layer. Moreover, the impregnation of the hydrophilic particles in the absorbent core may be accomplished as discussed more fully in application Ser. No. 10/725,574, and is performed prior to the application of the backing layer.

Methods for applying the apertured facing layer onto the absorbent core are described more fully in application Ser. No. 10/725,574.

It will be understood that while various embodiments are particularly described and illustrated herein, features of these embodiments may be combined in any manner consistent with the description provided herein to form additional embodiments and variations thereof not particularly described herein. As a result, it will be understood that the above described embodiments and methods are illustrative in nature, and that modifications thereof may occur to those skilled in the art. Accordingly, this invention is not to be regarded as limited to the embodiments disclosed herein, but is to be limited only as defined in the appended claims.

We claim:

1. A wound dressing defining bodyside and backside surfaces, comprising:
    a vapor-permeable backing layer having first and second surfaces, the backing layer defining a center portion and a border portion surrounding the center portion;
    a skin-adherent first facing layer formed from a silicone gel elastomer and having first and second surfaces, the second surface connected to the border portion along the first surface of the backing layer, the first facing layer consisting a shape defined only by the border portion of the backing layer;
    an absorbent core having first and second surfaces, the second surface of the absorbent core connected to the first surface of the backing layer; and
    a covering layer comprised of a polymeric film having first and second surfaces, and defining a plurality of apertures formed in a substantially uniform pattern, the second surface laminated adjacent to the first surface of the absorbent core, the covering layer having a center portion corresponding to the entirety of the absorbent core wherein the covering layer center portion forms a center portion of the bodyside surface;

a carrier layer interposed between the backing layer and the first facing layer, said carrier layer surrounding the center portion of the backing layer;

wherein the first surfaces of the first facing layer and the covering layer define the entirety of the bodyside surface of the wound dressing, the first facing layer and the covering layer are juxtaposed to one another with the first facing layer encircling the center portion of the covering layer.

2. The wound dressing according to claim 1, wherein the first surface of the polymeric film is not adherent to skin.

3. The wound dressing according to claim 1, wherein the polymeric film is a silicone sheet.

4. The wound dressing according to claim 3, wherein the first surface of the silicone sheet includes a detackifying substance.

5. The wound dressing according to claim 3, wherein the covering layer is liquid impervious and moisture permeable.

6. A wound dressing defining bodyside and backside surfaces, comprising:
  a vapor-permeable backing layer defining first and second surfaces, the backing layer defining a center portion and a border portion surrounding the center portion;
  a skin-adherent first facing layer defining first and second surfaces, the second surface connected to the border portion along the first surface of the backing layer, the first facing layer having a shape defined by the border portion of the backing layer;
  an absorbent core defining first and second surfaces, the second surface of the absorbent core secured to the first surface of the backing layer and generally within the boundaries of the center portion of the backing layer; and
  a carrier layer interposed between the backing layer and the first facing layer, said carrier layer surrounding the center portion of the backing layer, the carrier layer having a stiffness reinforcing the border portion of the backing layer relative the central portion of the backing layer;

wherein the first surfaces of the first facing layer and the absorbent core define the entirety of the bodyside surface of the wound dressing, the first facing layer and the absorbent core juxtaposed to one another with the first facing layer encircling the periphery of the absorbent core.

7. The wound dressing according to claim 6, herein the carrier layer is liquid impervious and moisture permeable.

8. The wound dressing according to claim 6, wherein the absorbent core comprises at least two layers of foam having different densities and absorption properties.

9. The wound dressing according to claim 6, wherein the second surface of the absorbent core is not adherent to skin.

10. The wound dressing according to claim 6, wherein the first facing layer and the carrier layer are laminated to one another.

11. The wound dressing according to claim 6, wherein the first facing layer is a pressure sensitive adhesive.

12. The wound dressing according to claim 6, wherein the first facing layer is a silicone-based compound.

13. The wound dressing according to claim 6, wherein the absorbent core comprises hydrophilic foam.

* * * * *